United States Patent [19]

Kobori et al.

[11] Patent Number: 4,981,972
[45] Date of Patent: Jan. 1, 1991

[54] PROCESS FOR PRODUCING OXAZOLONE DERIVATIVES

[75] Inventors: Yoshihiro Kobori, Kamakura; Hitoshi Yuasa; Mitsuo Matsuno, both of Yokohama; Tetsuo Satoh, Tokyo, all of Japan

[73] Assignee: Nippon Oil Co., Ltd., Tokyo, Japan

[21] Appl. No.: 357,401

[22] Filed: May 26, 1989

[30] Foreign Application Priority Data

Jun. 3, 1988 [JP] Japan .................................. 63-135615

[51] Int. Cl.$^5$ ........................................... C07D 263/42
[52] U.S. Cl. .................................................... 548/228
[58] Field of Search ........................................ 548/228

[56] References Cited

U.S. PATENT DOCUMENTS 4,339,589 7/1982 Steglich .............................. 548/228

OTHER PUBLICATIONS

Carter et al., Jour. Am. Chem. Soc., vol. 75, pp. 4705–4709 (1953).
Izv. Akad. Nauk. SSSR., Ser. Khim, 1970, 724.

Primary Examiner—Donald G. Daus
Attorney, Agent, or Firm—Bucknam and Archer

[57] ABSTRACT

A process for producing oxazolone derivatives, usable as important starting materials for medicines and pesticides, of the following general formula (III) by reacting a compound of the general formula (I) with a compound of the general formula (II) in the presence of an aliphatic tertiary amine:

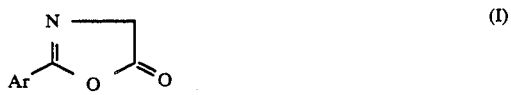

(I)

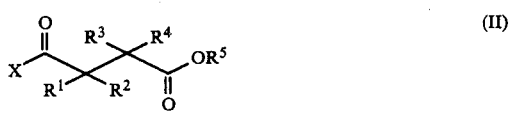

(II)

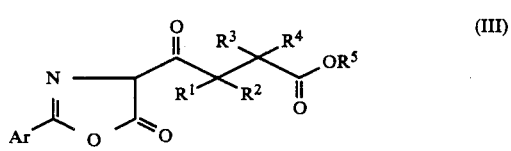

(III)

wherein Ar represents an aromatic hydrocarbon residue, $R^1$, $R^2$, $R^3$ and $R^4$ each represent a hydrogen atom, a halogen atom or an organic residue, $R^5$ represents a hydrocarbon residue and X represents a halogen atom.

1 Claim, No Drawings

PROCESS FOR PRODUCING OXAZOLONE DERIVATIVES

BACKGROUND OF THE INVENTION

1. Field of the Invention

The present invention relates to a process for producing oxazolone derivatives.

The oxazolone derivatives are used as intermediates for medicines and pesticides.

For example, compounds of the formula

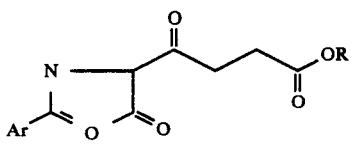

can be hydrolyzed under an acidic condition into δ-aminolevulinic acid (ALA) of the formula:

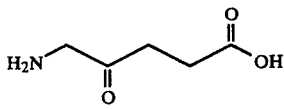

usable as intermediates for the biosynthesis of chlorophyll or heme or as herbicides.

2. Description of the Prior Art

It is known that the oxazolone derivatives of the general formula (III) are obtained by reacting a compound of the general formula (I) with a compound of the general formula (II) in the presence of γ-picoline (Izv. Akad. Nauk SSSR, Ser. Khim., 1970, 724).

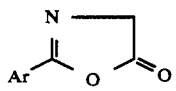  (I)

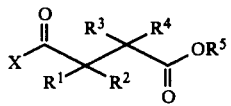  (II)

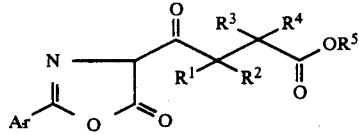  (III)

wherein Ar represents an aromatic hydrocarbon residue, $R^1$, $R^2$, $R^3$ and $R^4$ each represent a hydrogen atom, a halogen atom or an organic residue, $R^5$ represents a hydrogen residue and X represents a halogen atom.

Since γ-picoline is used in an amount sufficient for serving as the solvent in the above-described process, it must be recovered and reused to conduct this process on an industrial scale. Since however γ-picoline has a high boiling point and is soluble in water, a high recovering cost is required and the yield is unsatisfactory.

SUMMARY OF THE INVENTION

An object of the present invention is to provide a process for producing the compound (III) in a high yield at a low cost by reacting the compound (I) with the compound (II).

After intensive investigations of the process for producing the compound (III) by reacting the compound (I) with the compound (II) made for the purpose of overcoming the above described defects, the inventors have found that the compound (III) can be produced in a high yield by reacting the compound (I) with the compound (II) in the presence of a tertiary aliphatic amine and that the tertiary aliphatic amine can be easily recovered and reused. The present invention has been completed on the basis of this finding.

DETAILED DESCRIPTION OF THE INVENTION

The present invention relates to a process for producing oxazoline derivatives of the following general formula (III) by reacting a compound of the general formula (I) with a compound of the general formula (II) in the presence of an aliphatic tertiary amine:

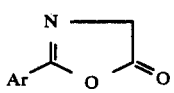  (I)

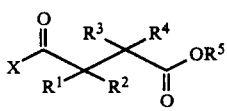  (II)

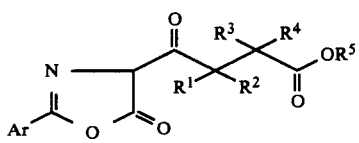  (III)

wherein Ar represents an aromatic hydrocarbon residue, $R^1$, $R^2$, $R^3$ and $R^4$ each represent a hydrogen atom, a halogen atom or an organic residue, $R^5$ represents a hydrocarbon residue and X represents a halogen atom.

Ar in the general formula (I) is preferably an aromatic hydrocarbon residue having 6 to 10 carbon atoms such as

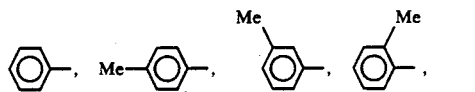

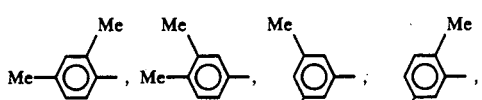

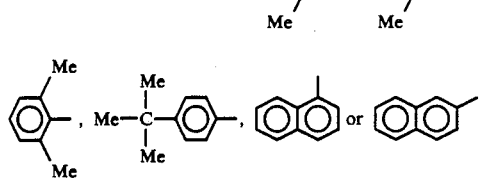

Among them, a phenyl group is particularly preferred. Me in the general formula (I) represents a methyl group.

The compounds of the formula (I) can be produced by a known process comprising, for example, treating a compound of the general formula (IV):

  (IV)

with a carboxylic acid anhydride such as acetic anhydride or an acyl halide such as acetyl chloride, benzoyl chloride or that of the formula (II). Therefore, it is possible to produce the compound (I) in situ and at the same time the compound (III) by reacting the compound (IV) with the compound (II) In this case, as a matter of course, 2 mol of the compound (II) is necessary, since one mol of the compound (II) is consumed for the production of the compound (I) and another mol thereof is consumed for the production of the compound (IV).

In the general formula (II), X represents a halogen atom, i.e. F, Cl, Br or I. Among them, Cl or Br is preferred. $R^1$ to $R^4$ each represent a hydrogen atom, a halogen atom or an organic residue, the halogen atom being F, Cl, Br or I and the organic residue being preferably a hydrocarbon group or a halogenated hydrocarbon group having 1 to 15 carbon atoms. The hydrocarbon groups include, for example, saturated hydrocarbon groups such as methyl, ethyl, propyl and butyl groups, aromatic hydrocarbon groups such as phenyl, benzyl and naphthyl groups, and unsaturated hydrocarbon groups such as vinyl and propenyl groups. The halogenated hydrocarbon groups are hydrocarbon groups having one or more of F, Cl, Br and I. They may contain hydrogen atoms or no hydrogen atoms. Examples of the halogenated hydrogen groups include $-CF_3$, $-CCl_3$, $-C_2F_5$, $-CH_2CF_3$, $-CH_2CH_2CF_3$,

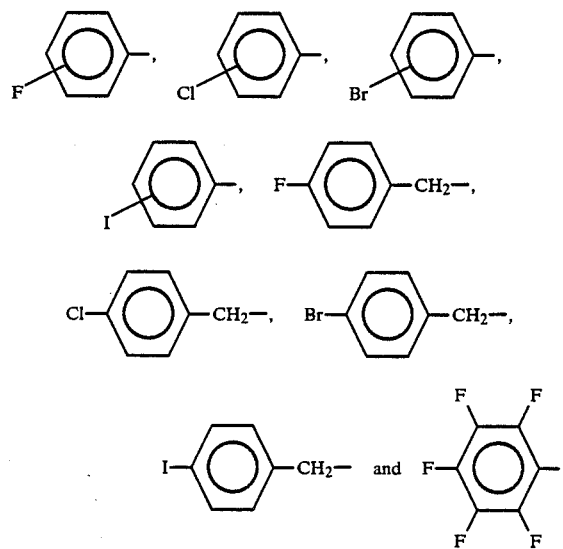

$R^5$ is preferably a hydrocarbon group having 1 to 15 carbon atoms. The hydrocarbon groups are those described above for $R^1$ to $R^4$.

The aliphatic tertiary amines used in the present invention are those represented by the general formula: $NR_3$ wherein R represents an alkyl group having 1 to 18, preferably 1 to 12 and particularly 1 to 6 carbon atoms. They include, for example, trimethylamine, triethylamine, tripropylamine and tributylamine. Among them trimethylamine and triethylamine are particularly preferred.

The compound (I) is reacted with the compound (II) in a molar ratio in the range of 0.8 to 1.2, preferably 0.9 to 1.1. When the molar ratio is outside this range, the amount of the starting material which is discarded without substantially participating in the reaction is increased unfavorably.

The aliphatic tertiary amine is used essentially for trapping an HX (X being a halogen) formed by the reaction of (I) with (II).

Therefore, it is preferred that the molar number of the aliphatic tertiary amine used is larger than the smaller molar number of (I) and (II) (hereinafter referred to as the basic molar number) for accelerating the reaction. When the aliphatic tertiary amine is used in at least 3 times, preferably at least 5 times and still preferably at least 10 times as much as the basic molar number, the yield of the compound (III) is remarkably improved. Although the upper limit of the amount of the aliphatic tertiary amine used is not particularly provided, an excess thereof is unnecessary. An amount 100 times as much as the basic molar number, particularly 50 times as much as that, will suffice.

Although the process of the present invention can be conducted without using any solvent, it is preferably conducted in the presence of a solvent. The solvent is not limited so far as the starting materials are soluble therein and it exerts no adverse effect on the reaction However, it is unnecessary that the starting materials be completely dissolved in the solvent under the reaction conditions and the reaction can be conducted even when part of the starting materials remain undissolved. The solvents usable herein include, for example, ethers such as diethyl ether, tetrahydrofuran and dioxane; halogenated hydrocarbons such as chloroform, dichloromethylene and dichloroethane; lactones such as $\gamma$-butyrolactone and $\gamma$-valerolactone; and aromatic hydrocarbons such as benzene, toluene and xylene. The amount of the solvent used is not particularly limited. It is usable in an amount of 0.05 to 20 parts by volume, preferably 0.5 to 10 parts by volume, per part by volume of the amine used.

Although a catalyst such as p-dimethylaminopyridine can be used for the reaction, a sufficient yield of (III) can be obtained without using it. When the catalyst is used, its amount is 1/1000 to ½, preferably 1/100 to 1/10 of the basic molar number.

The process of the present invention is conducted at a temperature in the range of $-100°$ to $50°$ C., preferably $-80°$ to $30°$ C.

[EXAMPLES]

The following Examples will further illustrate the present invention, which by no means limit the invention.

EXAMPLE 1

The reaction was conducted as described below. In all of the Examples, Ph represents a phenyl group, Me a methyl group, Et an ethyl group, Pr a propyl group and Bu a butyl group.

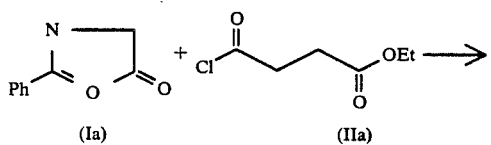

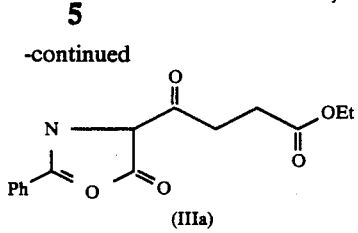

(IIIa)

3 g (18.6 mmol) of Ia, 0.12 g (0.99 mmol) of p-dimethylaminopyridine, 50 ml of dry THF and 29.3 g (290 mmol) of dry triethylamine were placed in a 300-ml three-necked flask. The flask was placed in a dry ice-/acetone bath and a mixture of 3.38 g (20.5 mmol) of IIa with 10 ml of THF was added dropwise thereto under stirring in 10 min. The mixture was stirred on the bath for 5 h and then the liquid temperature was gradually elevated. After stirring at room temperature for two days, 100 ml of ice/water containing 20 ml of concentrated hydrochloric acid was mixed therein. A beige solid thus precipitated was recovered by filtration and washed with water and methanol. After drying, 4.6 g (15.9 mmol, 85% yield) of IIIa which was substantially pure according to H-NMR was obtained.

EXAMPLE 2

The same procedure as that of Example 1 was repeated except that no p-dimethylaminopyridine was used. 3.34 g (11.5 mmol, 62% yield) of IIIa was obtained.

EXAMPLE 3

The same procedure as that of Example 1 was repeated except that THF was replaced with diethyl ether. 3.77 g/cm$^3$ (13.0 mmol, 70% yield) of IIIa was obtained.

EXAMPLE 4

The same procedure as that of Example 1 was repeated except that the dry ice/acetone bath was replaced with an ice bath containing common salt 2.96 g (10.2 mmol, 55% yield) of IIIa was obtained.

EXAMPLES 5 TO 7 the same procedure as that of Example 1 was repeated by varying the amount of triethylamine. The results are shown in Table 1.

TABLE 1

| Example | Et$_3$N g (mmol) | Yield of IIIa g (mmol) | Yield % |
|---|---|---|---|
| Example 5 | 3.6 (35.6) | 0.19 (0.65) | 3.5 |
| Example 6 | 14.5 (143) | 2.58 (8.9) | 48 |
| Example 7 | 21.8 (215) | 3.82 (13.2) | 71 |

EXAMPLE 8 AND 9

The same procedure as that of Example 1 was repeated except that triethylamine was replaced with tri(n-propyl)amine or tri(n-butyl)amine.
The results are shown in Table 2.

TABLE 2

| Example | Amine g (mmol) | Yield of IIIa g (mmol) | Yield % |
|---|---|---|---|
| Example 8 | n-Pr$_3$N 41.5 (290) | 3.77 (13.0) | 70 |
| Example 9 | n-Bu$_3$N 53.8 (290) | 3.50 (12.1) | 65 |

EXAMPLES 10 TO 14

The same procedure as that of Example 1 was repeated except that IIa was replaced with an acyl halide of a dicarboxylic monoester. The results are shown in Table 3.

According to the present invention, oxazolone derivatives usable as important starting materials for medicines and pesticides can be produced easily in high yields by using an aliphatic tertiary amine.

TABLE 3

| Example | Acyl halide | Amount | Product | Yield | Yield (%) |
|---|---|---|---|---|---|
| 10 | Cl-C(=O)-CH(CH$_3$)-CH$_2$-C(=O)-OMe | 3.38 g (20.5 mmol) | Ph-C(=N-)-O-... OMe | 3.68 g (12.7 mmol) | 62 |
| 11 | Br-C(=O)-CH$_2$-CH$_2$-C(=O)-OEt | 4.29 g (20.5 mmol) | III a | 4.21 g (14.6 mmol) | 71 |
| 12 | Cl-C(=O)-CH$_2$-CH(CH$_3$)-C(=O)-OMe | 3.38 g (20.5 mmol) | Ph-C(=N-)-O-... OMe | 2.08 g (7.2 mmol) | 35 |
| 13 | Cl-C(=O)-CH(Ph)-CH$_2$-C(=O)-OMe | 4.65 g (20.5 mmol) | Ph-C(=N-)-O-... Ph, OMe | 3.39 g (9.6 mmol) | 47 |

TABLE 3-continued

| Example | Acyl halide | Amount | Product | Yield | Yield (%) |
|---|---|---|---|---|---|
| 14 | 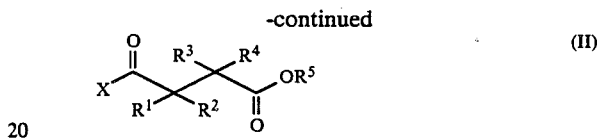 | 5.35 g (20.5 mmol) | 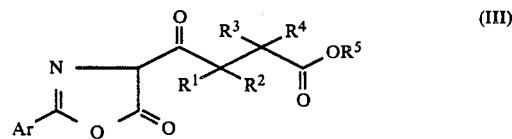 | 3.32 g (8.6 mmol) | 42 |

What is claimed is:

1. A process for producing an oxazolone derivative of general formula (III) by reacting a compound of formula (I) with a compound of formula (II) in the presence of an aliphatic tertiary amine of formula $NR_3$ wherein R is alkyl of 1 to 18 carbon atoms wherein the molar number of said aliphatic tertiary amine is at least 3 times as much as the smaller molar number of (I) and (II), at a temperature in the range of $-100°$ C. to $50°$ C. in the presence of a solvent:

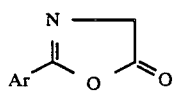 (I)

(II)

(III)

wherein Ar is an aromatic hydrocarbon residue, each of $R^1$, $R^2$, $R^3$, and $R^4$ is a hydrogen atom, a halogen atom or an organic residue, $R^5$ is a hydrocarbon residue and X is a halogen atom, said solvent is at least one member selected from the group consisting of ethers, halogenated hydrocarbons, lactones and aromatic hydrocarbons and in the presence of a catalyst which is p-dimethylaminopyridine, wherein the molar number of the tertiary amine is ten times as much as the smaller molar number of said compounds (I) and (II).

* * * * *